US009970924B2

(12) United States Patent
Vardjan

(10) Patent No.: US 9,970,924 B2
(45) Date of Patent: May 15, 2018

(54) MECHANISM AND DRUG TARGETS FOR REDUCING CELL EDEMA (NEUROPROTECTION) AND CYTOPLASMIC EXCITABILITY IN ASTROCYTES IN NORMAL AND PATHOLOGICAL STATES

(71) Applicant: CELICA D.O.O., Ljubljana (SI)

(72) Inventor: Nina Vardjan, Ljubljana (SI)

(73) Assignee: Celica Biomedical, Ljubljana (SI)

(*) Notice: Subject to any disclaimer, the term of this patent is extended or adjusted under 35 U.S.C. 154(b) by 0 days. days.

(21) Appl. No.: 14/900,656

(22) PCT Filed: Jun. 23, 2014

(86) PCT No.: PCT/EP2014/063193
§ 371 (c)(1),
(2) Date: Dec. 22, 2015

(87) PCT Pub. No.: WO2014/206948
PCT Pub. Date: Dec. 31, 2014

(65) Prior Publication Data
US 2016/0139112 A1 May 19, 2016

(30) Foreign Application Priority Data
Jun. 24, 2013 (EP) .................................. 13173446

(51) Int. Cl.
G01N 33/50 (2006.01)
G01N 33/68 (2006.01)
G01N 33/94 (2006.01)
A61K 31/138 (2006.01)
A61K 31/137 (2006.01)
A61K 31/19 (2006.01)
A61K 31/192 (2006.01)
A61K 31/436 (2006.01)
A61K 31/522 (2006.01)

(52) U.S. Cl.
CPC ....... *G01N 33/5058* (2013.01); *A61K 31/137* (2013.01); *A61K 31/138* (2013.01); *A61K 31/19* (2013.01); *A61K 31/192* (2013.01); *A61K 31/436* (2013.01); *A61K 31/522* (2013.01); *G01N 33/5041* (2013.01); *G01N 33/6896* (2013.01); *G01N 33/94* (2013.01); *G01N 2800/28* (2013.01)

(58) Field of Classification Search
None
See application file for complete search history.

(56) References Cited

U.S. PATENT DOCUMENTS 6,184,248 B1   2/2001   Lee et al.

FOREIGN PATENT DOCUMENTS

WO   2003/029411 A2   4/2003

OTHER PUBLICATIONS

Chesik et al., IGF-1 regulates cAMP levels in astrocytes through a beta2-adrenergic receptor—dependant mechanism, 2008, International Journal of Medical Sciences 5(5):240-243.*
Moldrich et al., Astrocyte mGlu2/3-mediated cAMP potentiation is calcium sensitive: studies in murine neuronal and astrocyte cultures, 2002, Neuropharmacology 43 (2002) 189-203.*
Song et al., Potassium Dependent Regulation of Astrocyte Water Permeability is Mediated by cAMP Signaling, Apr. 2012, PLoS ONE 7(4):1-8, e34936.*
Scott et al., Pathophysiology of cerebral oedema in acute liver failure, Dec. 28, 2013,World J Gastroenterol 19(48): 9240-9255.*
Perez et al., Dynamic reorganization of the astrocyte actin cytoskeleton elicited by cAMP and PACAP: a role for phosphatidyllnositol 3-kinase inhibition, 2005, European Journal of Neuroscience, vol. 21, pp. 26-32.*
International Search Report for corresponding Application No. PCT/EP2014/063193 dated Oct. 6, 2014.
Written Opinion for corresponding Application No. PCT/EP2014/063193 dated Oct. 6, 2014.
Potokar et al., "Regulation of AQP4 Surface Expression via Vesicle Mobility in Astrocytes", GLIA, vol. 61, No. 6, Mar. 18, 2013, pp. 917-928.
Fazzina et al., "The Protein Kinase C Activator Phorbol Myristate Acetate Decreases Brain Edema by Aquaporin 4 Downregulation after Middle Cerebral Artery Occlusion in the Rat", Journal of Neurotrauma, vol. 27, No. 2, Feb. 1, 2010, pp. 453-461.
Nicchia et al., "Actin Cytoskeleton Remodeling Governs Aquaporin-4 Localization in Astrocytes", GLIA, vol. 56, No. 16, Dec. 1, 2008, pp. 1755-1766.
Rutkowsky et al., "Effects of estradiol on ischemic factor-induced astrocyte swelling and AQP4 protein abundance", AJP-Cell Physiol, vol. 301, No. 1, Apr. 6, 2011, pp. C204-C212.
Miller et al., "Cerebral Protection by Barbiturates and Loop Diuretics in Head Trauma: Possible Modes of Action", Survey of Anesthesiology, vol. 56, No. 3, Apr. 1980, pp. 305-313.
Gregory et al., "Pentoxifylline and Propentofylline Prevent Proliferation and Activation of the Mammalian Target of Rapamycin and Mitogen Activated Protein Kinase in Cultured Spinal Astrocytes", Journal of Neuroscience Research, vol. 91, No. 2, Nov. 27, 2012, pp. 300-312.
Lee et al., "Prostaglandie E2 Stimulates Amyloid Precursor Protein Gene Expression: Inhibition by Immunosuppressants", The Journal of Neuroscience, Society for Neuroscience, vol. 19, No. 3, Feb. 1, 1999, pp. 940-947.
Slowik et al., "Involvement of formyl peptide receptors in receptor for advanced glycation end products (RAGE)—and amyloid beta 1-42-induced signal transduction in glial cells", Molecular Neurodegeneration, vol. 7, No. 1, Nov. 20, 2012, pp. 1-18.

(Continued)

*Primary Examiner* — John D Ulm
(74) *Attorney, Agent, or Firm* — Renner, Otto, Boisselle & Sklar, LLP

(57) ABSTRACT

The present invention pertains to a method for screening a compound useful in reducing astroglial edema, said method comprising: (i) providing a compound; (ii) bringing said compound in contact with an astrocyte; and (iii) determining the cAMP level in said astrocyte contacted with said compound; wherein said compound is identified as a compound useful in reducing astroglial edema, if the cAMP level in the astrocyte increases after contact. The present invention further pertains to an agent elevating the cAMP level in astrocytes for use in reducing astroglial edema.

4 Claims, 6 Drawing Sheets

(56) References Cited

OTHER PUBLICATIONS

Sheng et al., "Autophagy activation is associated with neuroprotection in a rat model of focal cerebral ischemic preconditioning", Autophagy Landes Bioscience Basic Research Paper, May 16, 2010, pp. 482-494.
Serkova et al., "Assessment of the Mechanism of Astrocyte Swelling Induced by the Macrolide Immunosuppressant Sirolimus Using Multinuclear Nuclear Magnetic Resonance Spectroscopy", Chemical Research in Toxicology, vol. 10, No. 2, Dec. 1, 1997, pp. 1359-1361.
Extended European Search Report for corresponding Application No. 13173446.9 dated Aug. 8, 2013.
Brandenburg et al., "Involvement of Formyl-Peptide-Receptor-Like-1 and Phospholipase D in the Internalization and Signal Transduction of Amyloid Beta 1-42 in Glial Cells", Neuroscience, vol. 156, No. 2, Oct. 2, 2008, pp. 266-276.
Brandenburg et al., "Internalization of PrP 106-126 by the formyl-peptide-receptor-like-1 in glial cells", Journal of Neurochemistry, vol. 101, No. 3, Nov. 20, 2006, pp. 718-728.
Consonni et al., "Inhibition of lipopolysaccharide-induced microglia activation by calcitonin gene related peptide and adrenomedullin", Molecular and Cellular Neuroscience, vol. 48, No. 2, Jul. 14, 2011, pp. 151-160.
De Keyser et al., "Astrocytes as potential targets to suppress inflammatory demyelinating lesions in multiple sclerosis", Neurochemistry International, vol. 47, No. 4, Nov. 1, 2010, pp. 446-450.
Ben-Shmuel et al., "Bradykinin decreases nitric oxide release from microglia via inhibition of cyclic adenosine monophosphate signaling", Peptides, vol. 40, Jan. 20 2013, pp. 133-140.
Ahmed et al., "GPR109A, GPR109B and GPR81, a family of hydroxy-carboxylic acid receptors", Trends in Pharmacological Sciences, vol. 30, No. 11, 2009, pp. 557-562.
Allaman et al., "A2B receptor activation promotes glycogen synthesis in astrocytes through modulation of gene expression", Am J Physiol Cell Physiol, vol. 284, Mar. 2003, pp. C696-C704.
Bergersen et al., "Is lactate a volume transmitter of metabolic states of the brain?", Frontiers in Neuroenergetics, vol. 4, Article 1, Mar. 19, 2012, pp. 1-6.
Bicknell et al., "Beta-Adrenergic and Opioid Receptors on Pituicytes Cultured From Adult Rat Neurohypophysis: Regulation of Cell Morphology", Brain Research Bulletin, Vo. 22, 1989, pp. 379-388.
Cureton et al., "A Different View of Lactate in Trauma Patients: Protecting the Injured Brain", Journal of Surgical Research, vol. 159, 2010, pp. 468-473.
Hatton et al., "Adrenalin Activation of beta 2-Adrenoceptors Stimulates Morphological Changes in Astrocytes (Pituicytes) Cultured From Adult Rat Neurohypophyses", Brain Research Bulletin, vol. 26, 1991, pp. 765-769.
Laureys et al., Astrocytic beta(2)-Adrenergic receptors: From physiology to pathology, Progress in Neurobiology, vol. 91, 2010, pp. 189-199.
Lee et al., "Stimulation of amyloid precursor protein synthesis by adrenergic receptors coupled to cAMP formation", Proc. Nat.l Acad. Sci. USA, vol. 94, May 1997, pp. 5422-5426.
Prebil et al., "Dynamic Monitoring of Cytosolic Glucose in Single Astrocytes", GLIA, vol. 59, 2011, pp. 903-913.
Ros et al., "Lactate Reduces Glutamate-Induced Neurotoxicity in Rat Cortex", Journal of Neuroscience Research, vol. 66, 2001, pp. 790-794.
Schurr et al., "Blockade of lactate transport exacerbates delayed neuronal damage in a rat model of cerebral ischemia", Brain Research, vol. 895, 2001, pp. 268-272.
Shain et al., "Morphology of Astroglial Cells is Controlled by Beta-Aadrenergic Receptors", The Hournal of cell Biology, vol. 105, Nov. 1987, pp. 2307-2314.
Wurm et al., "Involvement of A1 adenosine receptors in osmotic volume regulation of retinal glial cells in mice", Molecular Vision, 2009 pp. 1858-1867.
Borner et al., "FRET measurements of intracellular cAMP concentrations and cAMP analog permeability in intact cells", Nature Protocols, vol. 6, No. 4, 2011, pp. 427-438.
Ostroff et al., "Synapses lacking astrocyte appear in the amygdala during consolidation of Pavlovian threat conditioning", Journal of Comparative Neurology, vol. 522, No. 6, 2014, pp. 1-18.
Potokar et al., "Trafficking of astrocytic vesicles in hippocampal slices", Biochemical and Biophysical Research Communications, vol. 390, 2009, pp. 1192-1196.
Rodnight et al. "Morphological plasticity of rodent astroglia", Journal of Neurochemistry, vol. 124, 2013, pp. 263-265.
Schwartz et al., "Preparation and Characterization of Type 1 Astrocytes Cultured From Adult Rat Cortex, Cerebellum,. and Striatum", GLIA, vol. 5, No. 1, 1992, pp. 75-80.

* cited by examiner

MECHANISM AND DRUG TARGETS FOR REDUCING CELL EDEMA (NEUROPROTECTION) AND CYTOPLASMIC EXCITABILITY IN ASTROCYTES IN NORMAL AND PATHOLOGICAL STATES

This application is a national phase of International Application No. PCT/EP2014/063193 filed Jun. 23, 2014 and published in the English language, which claims priority to Application No. EP 13173446.9 filed Jun. 24, 2013.

FIELD OF THE INVENTION

The present invention relates to pharmaceutically active substance targets and mechanisms for reducing cell edema in astrocytes (nervous tissue protection). The invention also relates to reference compounds for elevating cAMP levels and to modulate astrocyte cytoplasmic excitability. This invention was made possible with experiments where cytosolic levels of two second messengers, cAMP ([cAMP]$_i$) and calcium ([Ca$^{2+}$]$_i$) were measured by fluorescence nanosensors in cultured astrocytes. These cells represent the most abundant glial cells in the brain and in some areas outnumber neurons. Current views hold that astrocytes are active partners in synaptic transmission, therefore the synapse has no longer two but three partners (tripartite synapse) in which cytoplasmic excitability of astrocytes plays a central role. They have been found to exhibit a special form of excitability (cytoplasmic excitability), where neurotransmitters elicit elevations in [Ca$^{2+}$]$_i$ which can in turn stimulate many processes, including the release of gliotransmitters by regulated exocytosis. The released gliotransmitters affect synaptic transmission, synaptogenesis and neuronal network activity. Most of recent studies focused into the understanding how astrocytes can be excited, very few addressed mechanisms that reduce astrocytic cytoplasmic excitability. However, by measuring cytosolic cAMP the results have shown that G-protein coupled receptors (GPCRs), such as β-adrenergic (β-AR) and lactate receptors (GPR81) are coupled to cAMP metabolism and play a role in physiological and pathophysiological processes. In this invention we show that elevations in [cAMP]$_i$ elicit a robust neuroprotective mechanism, measured as a reduction in hypotonicity-induced cell edema. In part this neuroprotective mechanism is associated with a cAMP-mediated reduction of cytoplasmic excitability of astrocytes and by recruitment of cytosolic glucose. These discoveries have a significant translational potential in the treatment of CNS pathologies such as trauma, cognitive deficits, autism, epilepsy, neuroinflammation and neurodegeneration, since all these pathologies are associated, at least at some stage, with brain parenchymal edema. Moreover, cAMP also affects glucose and glycogen metabolism in astrocytes, hence cAMP represents a link between GPCRs and glycogen metabolism which generates fuel and precursor molecules, such as glutamate.

BACKGROUND OF THE INVENTION

Astrocytes, the most abundant glial cells in the mammalian central nervous system (CNS), exhibit a special form of excitability (cytoplasmic excitability), characterized by elevations in the cytosolic free Ca$^{2+}$ concentration ([Ca$^{2+}$]$_i$), which are elicited by various transmitters and chemical messengers and affects many important cellular processes, including the exocytotic release of gliotransmitters, such as glutamate, ATP and peptides. In addition to Ca$^{2+}$ as a second messenger, cyclic adenosine monophosphate (cAMP) modulates a large variety of cellular functions and regulates numerous biological processes in the brain and in astrocytes. cAMP synthesis is mainly triggered by agonist-induced activation of transmembrane G protein-coupled receptors (GPCRs) and subsequent activation of adenylyl cyclases (AC) at the inner site of the plasma membrane. cAMP activates a limited number of effectors in the cell, primarily the cAMP-dependent protein kinase (PKA) which, by phosphorylating cytoplasmic and nuclear targets mediates many different functional effects, although signaling via cAMP-activated GTP-exchange protein Epac, and via cAMP-gated ion channels is also present. The cellular content of cAMP is tightly controlled by GPCRs via both ACs and cAMP-degrading phosphodiesterases (PDEs).

Astrocytes express several types of GPCRs (e.g. β-adrenergic receptors (β-AR), lactate receptors, metabotropic glutamate receptors, adenosine receptors, and others). β-ARs are abundantly present on astrocytes in both white and grey matter of the brain and regulate important astrocyte functions via activation/inhibition of cAMP dependent pathways. The activation of β-AR/cAMP signaling pathway in astrocytes by the "fight or flight response" neurotransmitter/hormone noradrenaline/adrenaline (NA/ADR), respectively, has been shown to promote rapid degradation of glycogen in astrocytes, which serves as the main brain energy reserve. In addition, NA may also elevate cytosolic glucose (Prebil et al., 2011) and glucose uptake via β-AR/cAMP signaling (Prebil et al., 2011) and increase glycogen content (Allaman et al., 2003). β-AR stimulation can induce the expression of cytokine IL-6 in astrocytes and neurotrophic factors, it can modulate glial inwardly rectifying potassium channels Kir, extracellular concentration of adenosine, and glutamate.

Impaired regulation of astrocytic β$_2$-AR/cAMP pathway is considered to contribute to the pathophysiology of several neurological conditions such as multiple sclerosis (Laureys et al., 2010) and Alzheimer's disease (Lee et al., 1997). Astroglial β-ARs are also functionally regulating astrocyte cellular morphology (Hatton et al., 1991). An increase in intracellular cAMP production upon β-AR stimulation induces astrocyte stellation, transformation from a flattened irregular morphology to a stellate, process-bearing morphology (Bicknell et al., 1989; Shain et al., 1987).

Lactate is considered to have two roles in the brain. It is a fuel and also likely acts on the plasma receptor GPR81 (Bergersen and Gjedde, 2012), originally discovered in adipose tissue, where GPR81 is highly expressed and serves to down-regulate the formation of cAMP, thereby curbing lipolysis and promoting energy storage. Interestingly, the neuroprotective role of lactate in the brain has been considered in ischemic, excitotoxic and mechanical insults (Cureton et al., 2010; Ros et al., 2001; Schurr et al., 2001). These effects are not easily explained solely by the role of lactate as a fuel, but indicate that lactate plays also a role in signalling, likely via the GPR81 receptor. However, direct real-time measurements of activation of this receptor in astrocytes have not been conducted. The results in this study show that GPR81 is present in astrocytes and that the activation of this receptor by lactate or 3-Chloro-5-hydroxybenzoic acid (3-Cl-5-HBA), an agonist of this receptor (Ahmed et al., 2009), elevates cytosolic cAMP and consequently also cytosolic glucose (Prebil et al., 2011).

The real-time dynamics of β-AR and GPR81 mediated cAMP signaling in live single astrocyte have not been reported. It is also unclear how the activation of β-ARs affects astrocyte morphology (cell area and perimeter). Genetically encoded FRET biosensors that enable direct monitoring of rapid changes in free cytosolic cAMP were developed recently. These sensors are based on downstream cAMP targets, including cAMP-dependent PKA, cAMP-gated ion channels, and cAMP-activated GTP-exchange protein Epac.

The cAMP level has never been used as a target for substances useful in the treatment of the pathophysiological states, such as CNS trauma, cognitive deficits, autism, neuroinflammation, epilepsy, neuroprotection, and neurodegenerative disorders, e.g. multiple sclerosis, Alzheimer's disease.

Central to the hypothesis of the tripartite synapse involves astrocyte cytoplasmic excitability. However, the knowledge of how this is attenuated is fragmental, especially in pathophysiological conditions. The response to traumatic CNS injury involves astroglial edema and likely also modifications in cytoplasmic excitability of cells. In cultured astrocytes hypotonic stimulation causes swelling and morphological changes due to membrane unfolding, not vesicle fusion (Pangrsic et al. 2006). Elevations in intracellular cAMP levels via purinergic and adenosine receptors were linked to reduced hypotonic swelling of retinal glial cells (Wurm et al., 2009). However, the involvement of cAMP signaling in astrocyte swelling has not been studied yet.

Against the background, it is an object of the present invention to provide targets for substances useful in the treatment of specific diseases, in particular of astroglial edema resulting from CNS trauma, cognitive deficit, autism, neuroinflammation, epilepsy and neurodegenerative disorders, such as multiple sclerosis, Alzheimer's disease.

SUMMARY OF THE INVENTION

The invention is based on the previously unrecognized relationship between the cAMP level and a range of specific neural disorders in which cell edema, altered cytoplasmic excitability and cytosolic glucose homeostasis are involved. For example, the inventor was the first to observe that in astrocytes β-AR agonists induce a rapid increase in [cAMP] i, as measured by the 10-15% FRET change with a time-constant of ~15 s.

Experiments conducted by the inventor revealed that the effect of ADR on cytosolic cAMP levels was concentration-dependent with a half-maximal response obtained at ~30 nM ADR, indicating the involvement of β-ARs, which could be blocked by specific antagonists. Within an hour this stimulation resulted in a 5-10% decrease in cell area and in a 30-50% increase in cell perimeter.

Experiments revealed that pretreatment of astrocytes by ADR reduces hypotonically induced cell swelling and that application of hypotonic medium to astrocytes induces oscillations in $[Ca^{2+}]$, which are attenuated by the presence of ADR. The inventor showed that ADR and cAMP-elevating agents that act through β-ARs reduce the number of exocytotic fusion events in astrocytes triggered by addition of ATP. ATP is known to increase $[Ca^{2+}]_i$. The inventor showed that addition of cAMP-elevating agents diminished the ATP-induced increase in $[Ca^{2+}]_I$ via cAMP mediated mechanism. Interestingly, these findings are linked to the activation of β-ARs, which also increases cytosolic glucose in astrocytes (Prebil et al., 2011).

The study shows that cultured astrocytes express GPCRs for lactate (GPR81 receptors). GPR81 receptor agonists increased $[cAMP]_i$ within 200 s after application.

From this new and hitherto unrecognized mechanisms—and from the fact that impaired regulation of astrocytic $β_2$-AR/cAMP pathway is considered to contribute to the pathophysiology of several neurological conditions such as multiple sclerosis, neuroinflammation and Alzheimer's disease and that astroglial β-ARs are also functionally regulating astrocyte cellular morphology via cAMP-mediated pathway, the inventor concluded that compounds acting on cAMP level (e.g. β-AR and GPR81 receptor agonists) according to the present invention may be substances useful in the treatment of traumatic CNS injury involving cell edema and substances which affect astrocytic cytoplasmic glucose and excitability, a process central in the concept of the tripartite synapse, where synaptic transmission is playing a role in neurodegenerative disorders such as multiple sclerosis, AD, cognitive disorders, epilepsy, neuroinflammation and others.

Thus, in one aspect the invention relates to a method for screening a compound (or for a compound) useful in reducing cell edema and/or in the treatment of a disease associated with astrocytic cytoplasmic hyperexcitability and/or cytosolic glucose homeostasis, said method comprising:
  (i) providing a compound;
  (ii) bringing said compound in contact with an astrocyte; and
  (iii) determining the cAMP level in said astrocyte contacted with said compound.

Preferred methods of screening are methods for screening for compounds useful in reducing cell edema.

In accordance with this aspect, said compound may be identified as a compound useful in reducing cell edema, and/or in the treatment of a disease associated with astrocytic cytoplasmic hyperexcitability and/or cytosolic glucose homeostasis, if the cAMP level in the astrocyte increases after contact.

In another aspect the invention pertains to an agent elevating the cAMP level in astrocytes for use in reducing cell edema and/or in the treatment of a disease associated with astrocytic cytoplasmic hyperexcitability and/or cytosolic glucose homeostasis. Preferably, the agent is for use in reducing of cell edema.

In a related aspect the invention pertains to the use of an agent elevating the cAMP level in astrocytes in the preparation of a medicament for use in reducing cell edema and/or in the treatment of a disease associated with astrocytic cytoplasmic hyperexcitability and/or cytosolic glucose homeostasis, preferably cell edema.

In a further related aspect the invention pertains to a method for reducing cell edema and/or for the treatment of a disease associated with astrocytic cytoplasmic hyperexcitability and/or cytosolic glucose homeostasis, said method comprising: administering to a subject in need thereof a therapeutic effective amount of an agent elevating the cAMP level in astrocytes.

It is understood that any details given herein in the context of the agent for use aspect equally applies to the above-mentioned use and method for treatment aspects.

Relative to FIGS. 1B-1G, note that the decline in the signal represents an increase in cAMP concentration and that an increase in the signal denotes a decrease in cAMP concentration.

FIGS. 2A to 2F show that adrenergic receptor agonists increase intracellular cAMP level in astrocytes in a concentration-dependent manner.

Figure 1A:
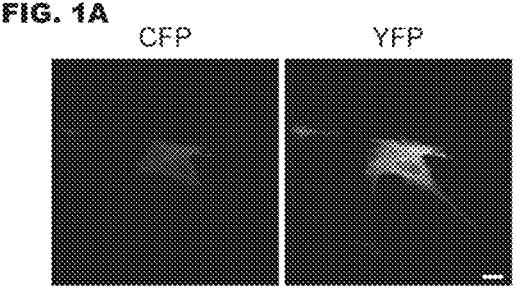
FIG. 1A shows comparative images of a single astrocyte transfected with Epac1-camps nanosensor responding to cAMP-elevating agents.
Figure 1B:
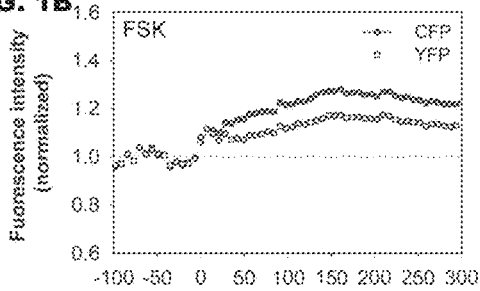
FIG. 1B shows Epac1-camps nanosensor expressed in a single astrocyte responding to cAMP-elevating agents, with change over time in the nanosensor measured in fluorescence intensity.
Figure 1C:
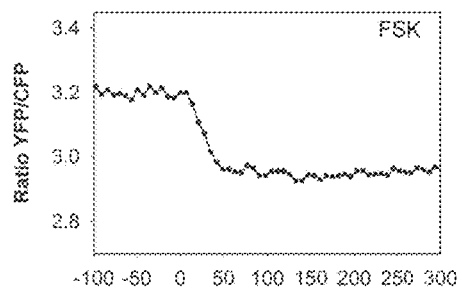
FIG. 1C shows Epac1-camps nanosensor expressed in a single astrocyte responding to cAMP-elevating agents, with change over time in the nanosensor measured in ratio of YFP to CFP.
Figure 1D:
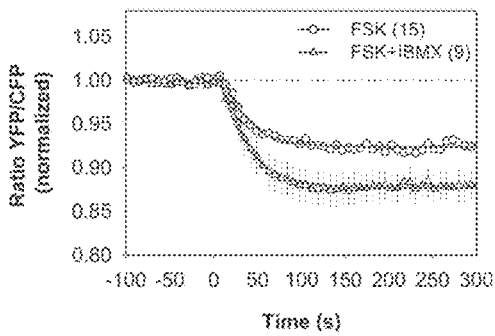
FIG. 1D shows fluorescence resonance energy transfer (FRET) measurements of cAMP in living primary astrocytes transfected with Epac1-camps; time-course of average Epac1-camps emission ratio after addition of 50 μM forskolin (FSK), 50 μM FSK with 200 μM 3-isobutyl-1-methylanxthine (IBMX), a phosphodiesterase inhibitor.
Figure 1E:
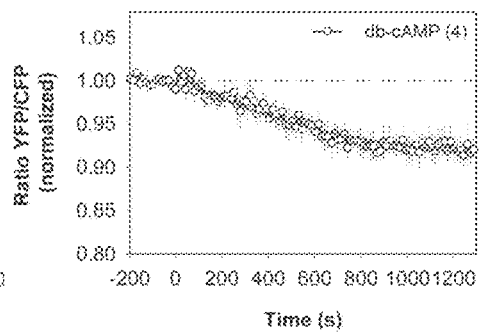
FIG. 1E shows fluorescence resonance energy transfer (FRET) measurements of cAMP in living primary astrocytes transfected with Epac1-camps; time-course of average Epac1-camps emission ratio after addition of 1 mM db-cAMP.
Figure 1F:
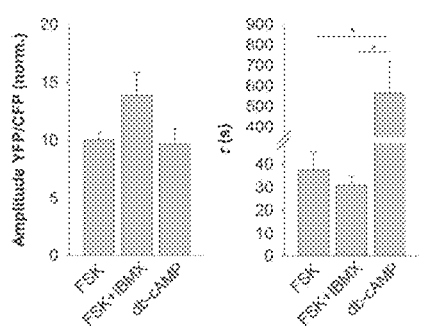
FIG. 1F shows fluorescence resonance energy transfer (FRET) measurements of cAMP in living primary astrocytes transfected with Epac1-camps.
Figure 1G:
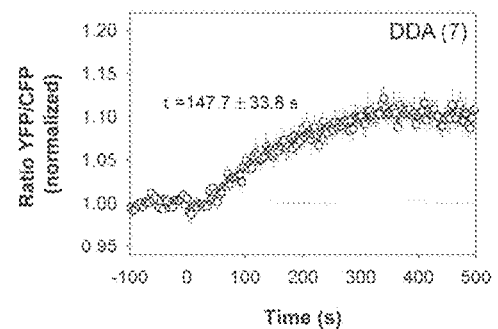
FIG. 1G shows fluorescence resonance energy transfer (FRET) measurements of cAMP in living primary astrocytes transfected with Epac1-camps; time-course of average Epac1-camps emission ratio after addition of 100 μM AC inhibitor 2',5'-dideoxiadenosine (DDA) at t=0.
Figure 2A:
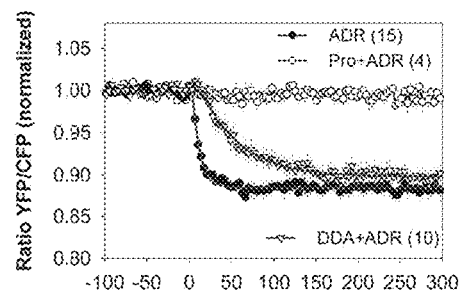

FIG. 2A shows time-course of Epac1-camps emission ratio after the addition of 1 μM adrenaline (ADR; t=0) in the absence and presence of 1 μM β-adrenergic antagonist propranolol (Pro) and 100 μM DDA.

Figure 2B:
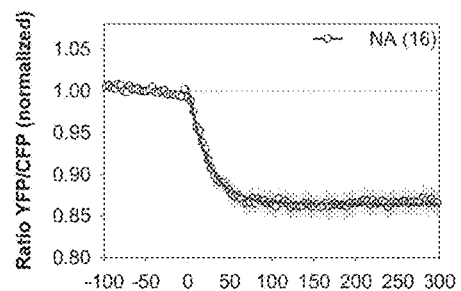

FIG. 2B shows time-course of Epac1-camps emission ratio after the addition of 1 μM noradrenaline (NA).

Figure 2C:
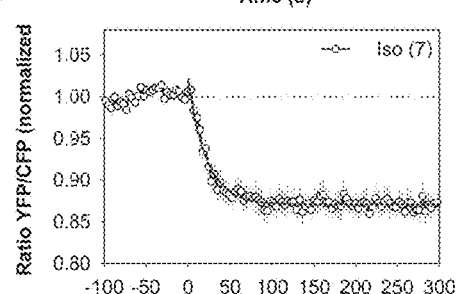

FIG. 2C shows time-course of Epac1-camps emission ratio after the addition of 1 μM β-adrenergic agonist isoprenaline (Iso; t=0).

Figure 2D:
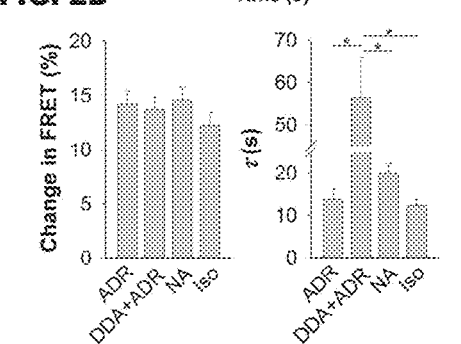

FIG. 2D shows average amplitude Epac1-camps FRET changes (left) and Average decay time-constants τ (right) for ADR, DDA+ADR, NA and Iso.

Figure 2E:
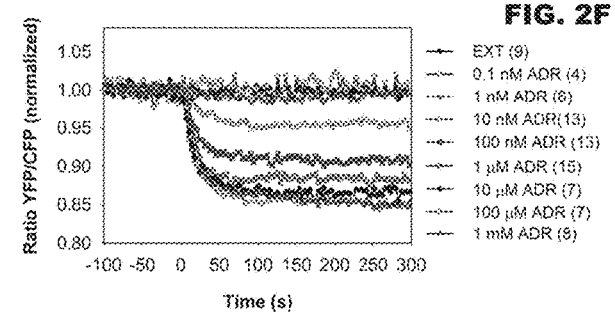

FIG. 2E shows representative time-course of Epac1-camps emission ratios upon the addition of different concentrations of ADR.

Figure 2F:
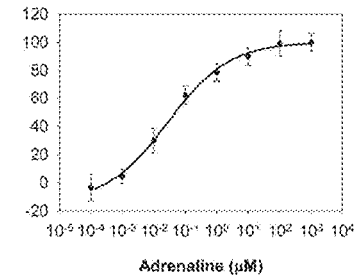

FIG. 2F shows dose-response relationship of maximum cAMP increase (represented as maximum YFP/CFP ratio) to ADR revealed a half-maximal response at around 30 nM ADR.

Figure 3A:
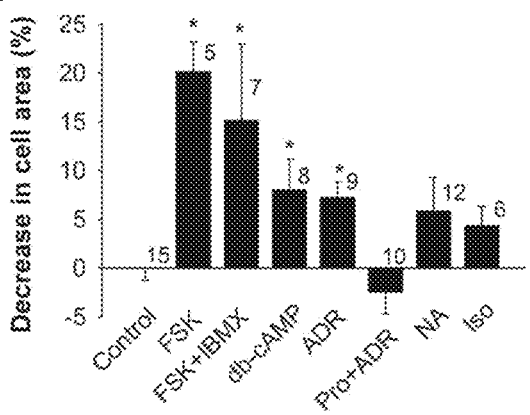

FIG. 3A shows that the cAMP-elevating agents decrease cell area in astrocytes, according to the invention. FIG. 3A shows the average effect of extracellular solution (Control), forskolin (FSK), forskolin and 3-isobutyl-1-methylanxthine (FSK+IBMX), dibutyryl cyclic adenosine monophosphate (db-cAMP), adrenaline (ADR), propranolol and adrenaline (Pro+ADR), noradrenaline (NA) and isoprenaline (Iso) on cell area in Epac1-camps transfected astrocytes.

Figure 3B:
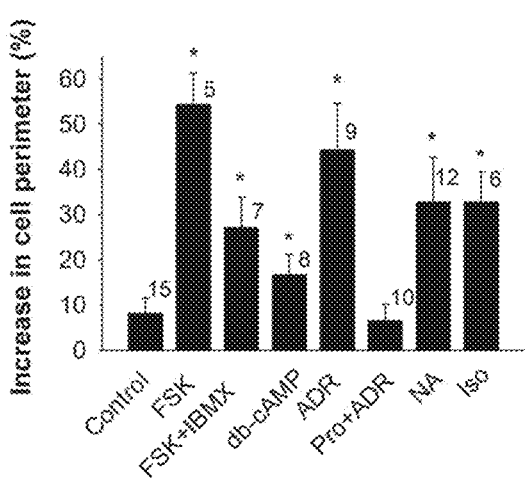

FIG. 3B shows that the cAMP-elevating agents increase cell perimeter in astrocytes, according to the invention. FIG. 3B shows the average effect of extracellular solution (Control), forskolin (FSK), forskolin and 3-isobutyl-1-methylanxthine (FSK+IBMX), dibutyryl cyclic adenosine monophosphate (db-cAMP), adrenaline (ADR), propranolol and adrenaline (Pro+ADR), noradrenaline (NA) and isoprenaline (Iso) on cell perimeter in Epac1-camps transfected astrocytes.

Figure 4A:
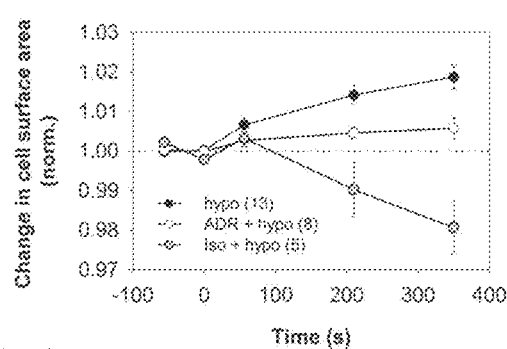
Figure 4B:
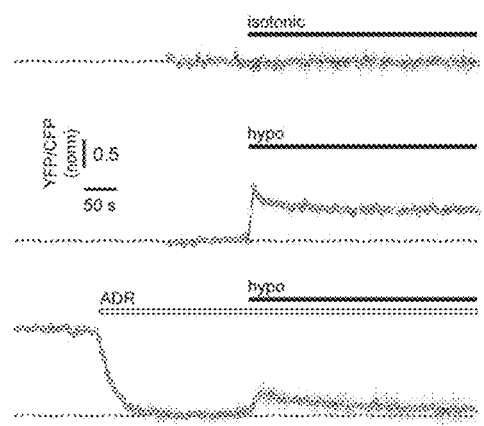
Figure 4C:
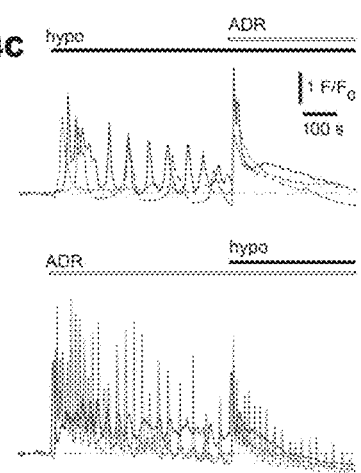
Figure 4C:
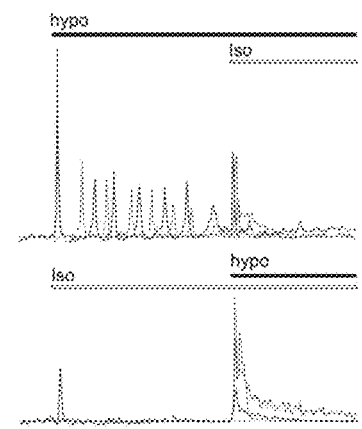

FIGS. 4A to 4C show that pretreatment of astrocytes by ADR or isoproterenol (Iso) reduces hypotonically-induced cell swelling and that ADR-pretreatment affects intracellular cAMP and $[Ca^{2+}]_i$.

FIG. 4A shows time-course of cell surface area changes induced by hypotonic media in control untreated cells and in ADR- and Iso-pretreated cells. Note the reduced swelling in the ADR- and Iso-pretreated cells.

FIG. 4B shows the effect of hypotonic medium on intracellular cAMP levels in astrocytes. Time-course of Epac1-camps emission ratio (YFP/CFP) induced by isotonic (n=9 cells) and hypotonic media (n=13 cells) in untreated astrocytes and by hypotonic medium in adrenaline (ADR) pretreated astrocytes (n=6 cells). Note that the increase in the signal at the time of hypotonic medium application indicates cell swelling and the consequent decrease (dilution) in cytosolic cAMP.

FIG. 4C shows the effect of hypotonic medium on intracellular $Ca^{2+}$ levels ($[Ca^{2+}]_i$) in astrocytes loaded with the calcium indicator Fluo-4 while stimulated with hypotonic medium (hypo) or 1 μM adrenaline (ADR) or 10 isoprenaline (Iso). Representative fluorescence intensity changes of the $[Ca^{2+}]_i$ expressed as the ratio ($F/F_0$) of three Fluo-4-loaded astrocytes stimulated either with hypotonic medium and subsequently with 1 μM ADR or 10 μM Iso and vice versa. Note that the application of hypotonicity elicited periodic elevations in $[Ca^{2+}]_i$, which ceased with the application of ADR or Iso. Furthermore, the application of ADR, but not Iso, also elicited periodic elevations in $[Ca^{2+}]_i$ and that the subsequent application of hypotonicity also resulted in the attenuation of the $[Ca^{2+}]_i$ signal—indicating inhibited astrocyte cytoplasmic excitability.

FIGS. 5A to 5D show that simultaneous treatment of astrocytes with ATP (an agonist that releases $Ca^{2+}$ from intracellular stores), and various cAMP-elevating agents diminishes ATP-induced increase in $[Ca^{2+}]_i$ and reduces the extent of ATP-triggered exocytotic fusion release events.

Figure 5A:
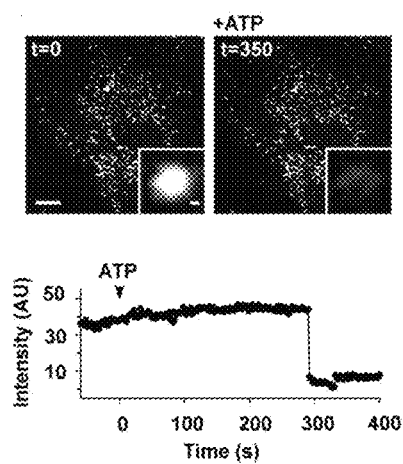

FIG. 5A's top graphical representation shows representative images showing Alexa Fluor$^{546}$ dextran-labeled vesicles in an astrocyte prior (left) and after (right) the stimulation with 1 mM ATP. FIG. 5A's bottom graphical representation shows time course of fluorescence intensity changes of an individual dextran-labeled vesicle marked with an arrowhead (top image), inset shows this vesicle enlarged, of which the intensity is suddenly reduced due to the release of the fluorescent dextran cargo (unitary release or fusion event).

Figure 5B:
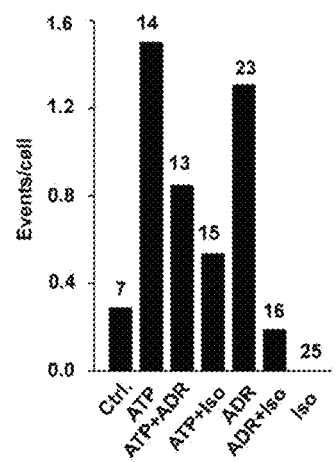

FIG. 5B demonstrates the number of unitary release fusion events per cell in cells treated with 1 mM ATP, 1 mM ATP+1 μM adrenaline (ADR), 1 mM ATP+10 μM isoprenaline (Iso), 1 μM ADR, 1 μM ADR+10 μM Iso, 10 μM Iso, and extracellular fluid as control (Ctrl.).

Figure 5C:
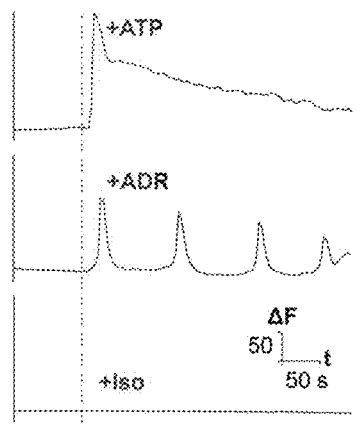
Figure 5D:
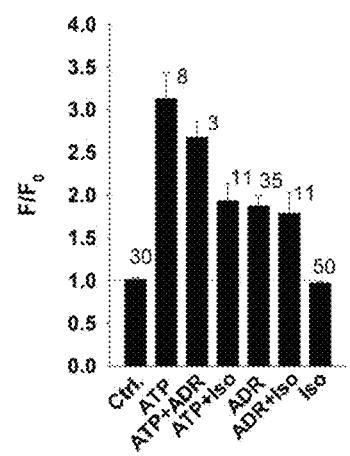

FIG. 5C shows representative time-dependent fluorescence intensity changes (ΔF) reporting changes in $[Ca^{2+}]_i$ in single Fluo-4 loaded astrocytes stimulated with 1 mM ATP, 1 mM ADR and 10 μM Iso. (FIG. 5D) Average fluorescence intensity changes ($F/F_0$) after stimulation with 1 mM ATP, 1 mM ATP+10 μM Iso, 1 mM ATP+1 μM ADR, 1 μM ADR, 1 μM ADR+10 μM Iso, 10 μM Iso, and extracellular fluid as control (Ctrl). Note that the simultaneous application of agents that elevate cAMP in astrocytes strongly attenuate the ATP-induced elevation in $[Ca^{2+}]_i$ indicating a cAMP-mediated inhibition of cytoplasmic excitability of astrocytes. This is then reflected in the reduced calcium-induced exocytotic release of dextran-loaded vesicle cargo.

FIGS. 6A to 6D show that astrocytes express GPR81 receptor for lactate and that treatment of astrocytes with GPR81 receptor agonists, lactate or 3-Chloro-5-hydroxy-benzoic acid (3-Cl-5-HBA), increases intracellular cAMP levels in astrocytes.

Figure 6A:
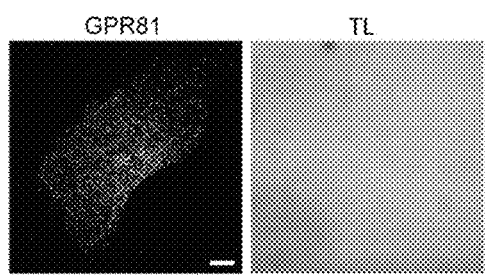

FIG. 6A shows cytochemical demonstration of the expression of GPR81 receptors in cultured rat astrocytes. Fluorescence image of an astrocyte immunostained with antibodies against GPR81 receptor (GPR81, left) and transmitted light (TL, right) image of the same cell.

Figure 6B:
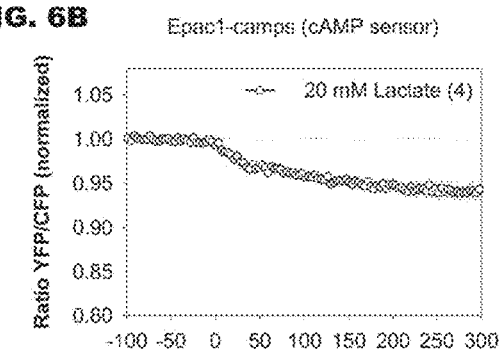

FIG. 6B shows FRET measurements of cAMP in living primary astrocytes transfected with Epac1-camps; time-course of average YFP/CFP emission ratio after addition of 20 mM lactate.

Figure 6C:
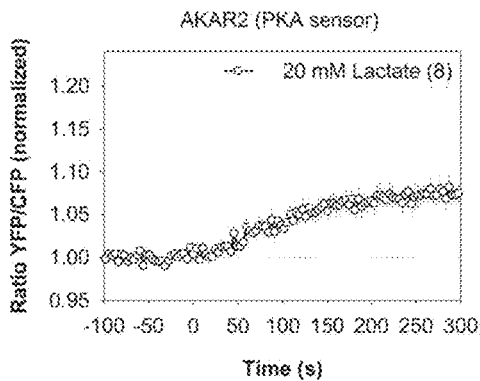

FIG. 6C shows FRET measurements of cAMP in living primary astrocytes transfected with AKAR2; time-course of average YFP/CFP emission ratio after addition of 20 mM lactate.

Figure 6D:
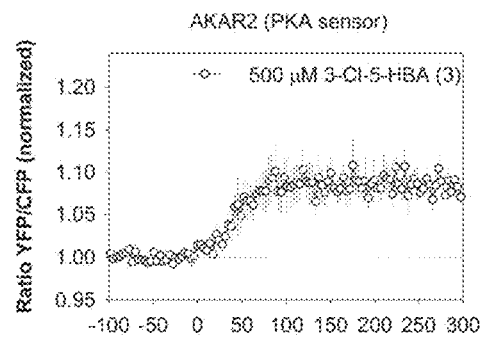

FIG. 6D also shows FRET measurements of cAMP in living primary astrocytes transfected with AKAR2; time-course of average YFP/CFP emission ratio after addition of 500 μM 3-Cl-5-HBA at t=0.

Note that Epac1-camps reports an increase in cytosolic cAMP as a decrease in the ratio signal, while the nanosensor AKAR2, reports the effect of cAMP-increased target phosphorylation by the elevation in the signal. These first direct measurements of lactate receptor activation by lactate and lactate receptor agonist 3-Cl-5-HBA, which result in an increase in cAMP, are consistent with the neuroprotective role of lactate in brain damage including ischemic, excitotoxic and mechanical insults (Cureton et al., 2010; Ros et al., 2001; Schurr et al., 2001), where the neuroprotective mechanism arises from the elevation in cAMP. As shown on (FIGS. 4A-4C) the elevation in cAMP reduced cell swelling and reduced cytoplasmic excitability of astrocytes.

DETAILED DESCRIPTION OF THE INVENTION

In one aspect the invention relates to a method for screening a compound useful in reducing cell edema and/or in the treatment of a disease associated with astrocytic cytoplasmic hyperexcitability and/or cytosolic glucose homeostasis, said method comprising:
  (i) providing a compound;
  (ii) bringing said compound in contact with an astrocyte; and
  (iii) determining the cAMP level in said astrocyte contacted with said compound.

Said compound may be identified as a compound useful in reducing cell edema (such as astroglial edema), and/or in the treatment of a disease associated with astrocytic cytoplasmic hyperexcitability and/or cytosolic glucose homeostasis, if the cAMP level in the astrocyte increases after contact.

The cAMP level may, for instance, be determined by fluorescence nanosensors in the astrocyte. In particular, the cAMP level may be determined by expressing the plasmid for FRET construct Epac1-camps or AKAR2. FRET construct are examined with immersion objective for fluorescent light and confocal microscope or other fluorescent microscope. Cells were excited at 458 nm or other suitable excitation wavelength of light and images are acquired every time interval. Emission spectra are collected from spectral detector or other suitable wavelength of light. Two-channel (CFP and YFP) images are generated from light detector. YFP and CFP fluorescence intensities are quantified within a region of interest selected for individual cell expressing Epac1-camps or AKAR2 using software. FRET signal is reported as the ratio of YFP to CFP fluorescence signal after subtracting the background fluorescence from both YFP and CFP signals. The change in FRET signals reflects change in [cAMP]i.

A disease associated with astrocytic cytoplasmic hyperexcitability and/or cytosolic glucose homeostasis in accordance to the invention may be a disease selected from the group consisting of epilepsy, intellectual disability, sleep disorders, CNS trauma, cognitive deficit, autism, neuroinflammation, and neurodegenerative disorders, such as multiple sclerosis, Alzheimer's disease, Parkinson's disease, and Huntington's chorea.

In another aspect the invention pertains to an agent elevating the cAMP level in astrocytes for use in reducing cell edema and/or in the treatment of a disease associated with astrocytic cytoplasmic hyperexcitability and/or cytosolic glucose homeostasis.

In a related aspect the invention pertains to the use of an agent elevating the cAMP level in astrocytes in the preparation of a medicament for use in reducing cell edema and/or in the treatment of a disease associated with astrocytic cytoplasmic hyperexcitability and/or cytosolic glucose homeostasis.

In a further related aspect the invention pertains to a method for reducing cell edema and/or for the treatment of a disease associated with astrocytic cytoplasmic hyperexcitability and/or cytosolic glucose homeostasis, said method comprising: administering to a subject in need thereof a therapeutic effective amount of an agent elevating the cAMP level in astrocytes.

The agent elevating the cAMP level in astrocytes in accordance with the invention may be an agonist for a G-protein coupled receptor. Such agonist may be an agonist for a β-adrenergic receptor (β-AR), and may be one or more (such as two) of the group consisting of adrenaline (ADR), noradrenalin (NA), dobutamine, dobutamine chloride, isoproterenol ($β_1$ and $β_2$), xamoterol, salbutamol, levosalbutamol, fenoterol, formoterol, metaproterenol, salmeterol, terbutaline, clenbuterol, isoetarine, pirbuterol, procaterol, ritodrine, arbutamine, befunolol, bromoacetylalprenololmenthan, broxaterol, cimaterol, cirazoline, denopamine, dopexamine, etilefrine, hexoprenaline, higenamine, indakaterol, salbutemol, isoxsuprine, mabuterol, methoxyphenamine, nylidrin, oxyfedrine, prenalterol, ractopamine, reproterol, rimiterol, tretoquinol, tulobuterol, zilpaterol, and zinerol.

Thus, the agent elevating the cAMP level for use in accordance with the invention may be adrenaline (ADR). A suitable concentration range for ADR to work therapeutically is, e.g.: from 0.1 μM to 10 μM.

The agent elevating the cAMP level for use in accordance with the invention may also be noradrenaline (NA).

An agonist for a G-protein coupled receptor in accordance with the invention may be an agonist for a lactate receptor, such as an agonist for the lactate receptor GPR81. Such agonist may be one or more (such as two) of the group consisting of lactate, such as D-lactate or L-lactate, hydroxybenzoic acid, such as 3-hydroxy benzoic acid, 3-hydroxy-5-substituted benzoic acid, such as 3-Chloro-5-hydroxybenzoic acid (3-Cl-5-HBA), 3-hydroxy butyrate, 3-hydroxyyoctanoate, 3H-imidazo[4,5-b]pyridin-5-ol derivatives.

Accordingly, the agent elevating the cAMP level in accordance with the invention may be lactate. The agent elevating the cAMP level in accordance with the invention may thus be D-lactate. The agent elevating the cAMP level in accordance with the invention may also be L-lactate. A suitable concentration range for lactate to work therapeutically is, e.g.: from 0.1 mM to 40 mM.

The agent elevating the cAMP level in accordance with the invention may also be 3-Chloro-5-hydroxybenzoic acid (3-Cl-5-HBA). A suitable concentration range for 3-Chloro-5-hydroxybenzoic acid (3-Cl-5-HBA) to work therapeutically is, e.g.: from 0.01 mM to 10 mM.

The agent elevating the cAMP level in astrocytes may also be a phosphodiesterase (PDE) inhibitor. The PDE inhibitor may be a nonselective PDE inhibitor, such as caffeine, aminophylline, 3-isobutyl-1-methylxanthine, paraxanthine, pentoxifylline, theobromine, or theophylline. The PDE inhibitor may also be PDE1 selective inhibitor, such as vinpocetine. The PDE inhibitor may also be a PDE2 selective inhibitor, such as erythro-9-(2-hydroxy-3-nonyl)adenine, BAY 60-7550, oxindole, or PDP (9-(6-Phenyl-2-oxohex-3-yl)-2-(3,4-dimethoxybenzyl)-purin-6-one). The PDE inhibitor may also be a PDE3 selective inhibitor, such as inamrinone, milrinone, enoximone, or cilostazol. The PDE inhibitor may also be a PDE5 selective inhibitor, such as mesembrine, rolipram, ibudilast, piclamilast, rolipram, luteolin, drotaverine, or roflumilast.

Accordingly, the PDE inhibitor may be one or more (such as two) of the group consisting of caffeine, aminophylline, 3-isobutyl-1-methylxanthine, paraxanthine, pentoxifylline, theobromine, theophylline, vinpocetine, erythro-9-(2-hydroxy-3-nonyl)adenine, BAY 60-7550, oxindole, inamrinone, PDP (9-(6-Phenyl-2-oxohex-3-yl)-2-(3,4-dimethoxybenzyl)-purin-6-one), milrinone, enoximone, cilostazol, mesembrine, rolipram, ibudilast, piclamilast, rolipram, luteolin, drotaverine, and roflumilast.

The agent elevating the cAMP level in accordance with the invention may also be rapamycin. A suitable concentration range for rapamycin to work therapeutically is, e.g.: from 0.001 µM to 100 µM.

The cell edema to be reduced in accordance with the invention may be astroglial edema.

The disease associated with astrocytic cytoplasmic hyperexcitability and/or cytosolic glucose homeostasis to be treated in accordance with the invention may be a disease selected from the group consisting of epilepsy, intellectual disability, sleep disorders, CNS trauma, cognitive deficit, autism, neuroinflammation, and neurodegenerative disorders, such as multiple sclerosis, Alzheimer's disease, Parkinson's disease, and Huntington's chorea.

Generally, the concentration range of an agent elevating the cAMP level in accordance with the invention to work therapeutically may be: from 0.001 µM to 100 mM, such as from 0.001 µM to 40 mM, from 0.001 µM to 10 mM, from 0.001 to 1 mM, from 0.001 µM to 100 µM, from 0.001 µM to 10 µM, from 0.01 µM to 100 µM, from 0.1 µM to 100 mM, from 0.1 µM to 40 mM, from 0.1 µM to 10 mM, from 0.1 µM to 1 mM, from 0.1 µM to 100 µM, from 0.1 µM to 10 µM, from 1 µM to 100 mM, from 1 µM to 40 mM, from 1 µm to 10 mM, from 1 µM to 1 mM, from 1 µM to 100 µM, from 1 µM to 10 µM, from 0.01 mM to 100 mM, from 0.01 mM to 40 mM, from 0.01 mM to 10 mM, from 0.01 mM to 1 mM, from 0.01 mM to 0.1 mM, from 0.1 mM to 100 mM, from 0.1 mM to 40 mM, from 0.1 mM to 10 mM, from 0.1 mM to 1 mM, from 1 mM to 100 mM, from 1 mM to 40 mM, from 1 mM to 10 mM, from 1 mM to 5 mM, from 10 mM to 100 mM, or from 10 mM to 40 mM.

FIG. 1 shows that Epac1-camps responds to cAMP-elevating agents in astrocytes. (a) FRET measurements of cAMP in living primary astrocytes transfected with Epac1-camps. CFP and YFP channel images of a representative astrocyte expressing Epac1-camps recorded by confocal microscopy. Below are time-dependent changes of Epac1-camps FRET donor (YFP) and acceptor (CFP) following their application of 50 µM forskolin (FSK) at t=0. Traces illustrate the average fluorescence intensity of CFP and YFP signal for the shown cell. Note that the CFP and YFP fluorescence signals moved in the opposite directions, YFP signal decreased and CFP signal increased after stimulation with FSK. (b) Time-course of Epac1-camps emission ratio after stimulation with 50 µM FSK. Note the rapid monophasic decline in FRET signal (represented as ratio YFP/CFP) after FSK stimulation reflecting the increase in intracellular cAMP levels. (d-e, g) Time-course of average Epac1-camps emission ratio after addition of (c) 50 µM FSK, 50 µM FSK with 200 µM IBMX, (d) 1 mM db-cAMP and (f) 100 µM AC inhibitor 2',5'-dideoxiadenosine (DDA) at t=0. Data are expressed as the YFP/CFP fluorescence emission ratio normalized to the baseline ratio values (ratio YFP/CFP). Numbers in the brackets depict numbers of independent experiments. Single exponential decay/rise functions were fitted to the curves. (f) Average amplitude of Epac1-camps FRET changes (left) and decay time constants τ (right) for FSK, FSK with IBMX, and db-cAMP. Changes in FRET are expressed as percents relative to the initial values. Note that the addition of PDE inhibitor IBMX increased Epac1-camps response to AC activator FSK. Data shown are in the format average±s.e.m. Scale bar: 20 µm.

FIG. 2 depicts an example that adrenergic receptor agonists increase intracellular cAMP levels in astrocytes in a concentration dependent manner. (a-c) Time-course of Epac1-camps emission ratio after the addition of 1 µM adrenaline (ADR; t=0) in the absence (black circle) and presence (white circle) of 1 µM β-adrenergic antagonist propranolol (Pro) and 100 µM DDA (down-triangle), and after the addition of (b) 1 µM noradrenaline (NA), and (c) 1 µM β-adrenergic agonist isoprenaline (Iso; t=0). Note that ADR triggered FRET response exhibited slower decay kinetics in the presence of DDA and is completely prevented in the presence of Pro. (d) Average amplitude Epac1-camps FRET changes (left) and average decay time-constants τ (right) for ADR, DDA+ADR, NA and Iso. Changes in FRET are expressed as percents relative to the initial values. (e) Representative time-course of Epac1-camps emission ratios upon the addition of different concentrations of ADR. (f) Dose-response relationship of maximum cAMP increase (represented as maximum YFP/CFP ratio) to ADR. The concentration of ADR at which 50% of maximum cAMP increase was observed ($EC_{50}$) is 29±0.10 nM. Data in (a-c, e) are expressed as the YFP/CFP fluorescence emission ratio normalized to the average baseline ratio values (ratio YFP/CFP). Numbers in the brackets depict numbers (n) of independent experiments. Each data represents average±s.e.m of n-independent experiments.

FIG. 3 provides an example of the cAMP-elevating agents that decrease cell area and increase cell perimeter in astrocytes. (a,b) Average effect of extracellular solution (Control), forskolin (FSK), FSK and 3-isobutyl-1-methyl-anxthine (FSK+IBMX), dibutyryl cyclic adenosine monophosphate (db-cAMP), adrenaline (ADR), propranolol and ADR (Pro+ADR), noradrenaline (NA) and isoprenaline (Iso) on cell area (a) and cell perimeter (b) in Epac1-camps transfected astrocytes. Bars represent average±s.e.m. Asterisk indicates a statistical difference (paired Students t-test, *p<0.05).

FIG. 4 shows that pretreatment of astrocytes by ADR or Iso reduces hypotonically induced cell swelling and affects intracellular cAMP and $Ca^{2+}$ levels. (a) Time-course of cell surface area changes induced by hypotonic media in control untreated cells (hypo, n=13 cells). in adrenaline (ADR) and isoprenaline (Iso) pretreated cells (ADR+hypo (n=8 cells)

and Iso+hypo (n=5 cells), respectively). Hypotonic stimulation induced an increase in cell surface area, indicating cell swelling, which was reduced in ADR- and Iso-pretreated cells. (b) The effect of hypotonic medium on intracellular cAMP levels in astrocytes. Time-course of Epac1-camps cAMP emission ratio (YFP/CFP) induced by isotonic (n=9 cells) and hypotonic medium (n=13 cells) in untreated astrocytes and by hypotonic medium in ADR pre-treated astrocytes (n=6 cells). FRET response increased upon hypotonic stimulation in control and ADR-treated cells, reporting decrease in intracellular cAMP levels. The increase in FRET response upon hypotonic stimulation was followed by a minor decline, but persisted at the elevated level throughout recordings. The increase in FRET response to hypotonic medium in ADR pre-treated cells was reversible and slowly declined to the baseline. (c) The effect of hypotonic medium on intracellular $Ca^{2+}$ levels in astrocytes. Astrocytes were loaded with a calcium indicator Fluo-4 and stimulated with hypotonic medium (hypo) or 1 µM ADR. (a-b) Representative fluorescence intensity changes of a calcium signal ($F/F_0$) in three Fluo-4 loaded astrocytes stimulated either with hypotonic medium and subsequently with 1 µM ADR or 10 µM Iso and vice versa. Note that hypotonic medium and ADR induced oscillations in intracellular calcium levels, but not Iso. The oscillations were more frequent in ADR— than in hypotonic medium-stimulated cells. Simultaneous treatment of cells with ADR and hypotonic medium or Iso and hypotonic medium resulted in a transient increase in intracellular calcium levels, which was followed by a decline to basal levels. Time of stimuli is indicated with black (hypo) and white (ADR or Iso) lines.

FIG. 5 shows that cAMP-elevating agents reduce astrocyte cytoplasmic excitability. Figure shows that simultaneous treatment of astrocytes with ATP and various cAMP elevating agents diminishes ATP-induced increase in intracellular $Ca^{2+}$ levels and reduces the number of ATP triggered exocytotic fusion release events. (a, top) Representative image showing Alexa Fluor$^{546}$ dextran-labeled vesicles in astrocyte prior (left) and after (right) stimulation with 1 mM ATP. Note the disappearance/destaining of a dextran-labeled fluorescence spot (arrowhead) after the addition of ATP, indicating vesicle fusion with the plasma membrane and the subsequent release of dextran to the extracellular space. Insets show magnification of the area with the vesicle undergoing fusion. Scale bars: 10 µm, 2 µm (insets). (a, below) Time-course of fluorescence intensity changes of individual dextran-labeled vesicle marked with an arrowhead above. Vesicle fusion with the plasma membrane and the vesicle cargo discharge resulted as a rapid decline in fluorescence intensity (<2 s) (b) Number of fusion events per cell in cells treated with 1 mM ATP, 1 mM ATP+1 µM adrenaline (ADR), 1 mM ATP+10 µM isoprenaline (Iso), 1 µM ADR, 1 µM ADR+10 µM Iso, 10 µM Iso, and extracellular fluid as control (Ctrl.). The numbers above the bars indicate the number of cells analysed. Number of fusion events is diminished when cells were simultaneously treated with Iso or ADR. (c) Representative fluorescence intensity changes of a calcium signal (ΔF) in single Fluo-4 loaded astrocytes stimulated with 1 mM ATP, 1 mM ADR and 10 µM Iso. Time of stimuli is indicated with a dotted line. Note that ADR and ATP induced changes in intracellular $Ca^{2+}$ levels, whereas Iso does not. (d) Average fluorescence intensity changes normalized to baseline fluorescence ($F/F_0$) and observed within first 100 s (as indicated with grey shade in (c)) after stimulation with 1 mM ATP, 1 mM ATP+10 µM Iso, 1 mM ATP+1 µM ADR, 1 µM ADR, 1 µM ADR+10 µM Iso, 10 µM Iso, and extracellular fluid (Ctrl). Note that intracellular $Ca^{2+}$ levels are increased after addition of ATP or ADR, whereas no significant difference in intracellular calcium is detected upon addition of Iso or extracellular fluid (Ctrl.). Simultaneous stimulation of cells with ATP and ADR or Iso diminishes the elevation in cytosolic calcium levels. The numbers above the bars indicate the number of Fluo-4 labeled cells analysed. Error bars indicate average±s.e.m.

FIG. 6 shows that astrocytes express GPR81 receptor for lactate and that the treatment of astrocytes with GPR81 receptor agonists, endogenous lactate or exogenous 3-Chloro-5-hydroxybenzoic acid (3-Cl-5-HBA), a specific agonist for GPR81, increases intracellular cAMP levels in astrocytes. (a) Expression of GPR81 receptors in cultured rat astrocytes. Fluorescence image of astrocyte cell immunostained with antibodies against GPR81 receptor (GPR81) and transmitted light (TL) image of the same cell. Scale bar: 20 µm. (b-d) FRET measurements of cAMP in living primary astrocytes transfected with (b) Epac1-camps and (c-d) AKAR2 cAMP nanosensors. Time-course of average YFP/CFP emission ratio after addition of (b-c) 20 mM lactate and (d) 500 µM 3-Cl-5-HBA at t=0. Data are expressed as the YFP/CFP fluorescence emission ratio normalized to the baseline ratio values (ratio YFP/CFP). Numbers in the brackets depict the number of independent experiments. Note that the increase in intracellular cAMP levels after stimulation in (b) is reflected by the rapid monophasic decline in FRET signal (ratio YFP/CFP) and in (c,d) by monophasic uprise in FRET signal. Each data represents mean±s.e.m.

The invention is now further illustrated with reference to the following non-limiting examples.

EXAMPLES

Example 1

Cultured astrocytes, e.g. isolated as previously described by Schwartz & Wilson (Glia. 1992; 5(1):75-80) or any other cell type isolated from animal tissues or clonal cell lines derived from human or animal sources are seeded onto coverslips and maintained in an adequate cell cultured medium. All chemicals were from Sigma Aldrich (St. Louis, Mo., USA) unless otherwise noted.

Astrocytes expressing Epac1-camps or AKAR2 FRET construct were examined with a Plan NeoFluoar 40×/1.3 Oil DIC immersion objective (Carl Zeiss, Jena, Germany) and 2-fold zoom factor using Zeiss LSM510 META confocal microscope (Carl Zeiss, Jena, Germany). Cells were excited at 458 nm and images (512×512) were acquired every 3.5 s or 7 s using Lambda stack acquisition. Emission spectra were collected from META detector in eight channels (lambda stack) ranging from 470 nm to 545 nm, each with a 10.7-nm width. Two-channel (CFP and YFP) images were generated from lambda stacks by analytical software "Extract channels". Channels with emission spectra 470- and 481-nm and emission spectra 513-, 524-, and 534-nm were extracted to CFP channel and YFP channel, respectively. YFP and CFP fluorescence intensities were quantified within a region of interest selected for individual cell expressing Epac1-camps or AKAR2 using LSM 510 META software. In the graphs, FRET signal is reported as the ratio of YFP to CFP fluorescence signal after subtracting the background fluorescence from both YFP and CFP signals using Sigma Plot. The values of FRET signals were normalized (set to 1.0) at the onset of the experiments. The decrease in FRET signals reflects an increase in [cAMP]i.

Initially, astrocytes were kept in standard extracellular solution (10 mM Hepes/NaOH, pH 7.2, 10 mM D-glucose, 131.8 mM NaCl, 1.8 mM CaCl2, 2 mM MgCl2, and 5 mM KCl) and then treated with various reagents following a 100 s baseline: 50 µM forskolin (FSK), 200 µM 3-isobutyl-1-methylxan-thine (IBMX; a nonspecific inhibitor of cAMP PDEs), 1 mM dibutyryl-cAMP (db-cAMP; a membrane-permeable derivative of cAMP), 100 µM 2',5'-dideoxiadenosine (DDA; AC inhibitor), 1 µM adrenaline (ADR; α- and β-adrenergic receptor agonist), 1 µM noradrenaline (NA; α- and β-adrenergic receptor agonist), 1 µM isoprenaline (Iso; β-adrenergic receptor agonist), and 1 µM propranolol (Pro; β-adrenergic receptor antagonist), 20 mM Sodium L-lactate (lactate; GPR81 receptor endogenous agonist). 500 µM 3-Chloro-5-hydroxybenzoic acid (3-Cl-5-HBA; GPR81 receptor exogenous agonist). In hypotonic stimulation experiments, cells in standard extracellular solution were treated with distilled $H_2O$ to ~60% of control (standard extracellular solution) osmolarity. Osmolarity was measured by using a freezing point osmometer Osmomat030 (Gonotech GmbH, Berlin, Germany).

Example 2

This example shows the analysis of FRET ratio changes.

The changes in YFP/CFP fluorescence emission ratio were normalized to baseline ratio values. Single-exponential ($F=F_0+c\times\exp(-t/\tau)$) decay functions or single-exponential rise to maximum functions ($F=F_0+c\times(1-\exp(-t/\tau))$) were fitted to the diagrams with YFP/CFP fluorescence emission ratios using SigmaPlot. The time-constant ($\tau$) and YFP/CFP emission ratio amplitudes (c) were determined from the fitted curves. F is YFP/CFP emission ratio at time t, $F_0$ is baseline YFP/CFP emission ratio, c is YFP/CFP emission ratio amplitude of $F_{(t=0)}-F_0$, and $\tau$ is the time constant of individual exponential component. The goodness of the exponential fits was judged from the calculated coefficient of determination, $R^2$.

In dose-dependence studies, maximum YFP/CFP ratio response was calculated by subtracting the average YFP/CFP ratio measured during the last 100 s after stimulation from the average YFP/CFP ratio measured during the first 100 s before stimulation (baseline). An average of maximum YFP/CFP emission ratio response was determined for each concentration of ADR. Four parameter logistic equation ($y=y_{min}+(y_{max}-y_{min})/1+(x/EC_{50})^{-Hillslope}$) was used to fit the dose-dependent curve in SigmaPlot (Systat Software) and to determine the $EC_{50}$ value. $y_{min}$ is minimum response (bottom of the curve), $y_{max}$ is maximum response (top of the curve), $EC_{50}$ is median effective concentration, and Hill slope characterizes the slope of the curve at its midpoint.

LSM 510 Meta software was used to measure cell area and perimeter of isolated Epac1-camps positive astrocytes before and after treatment of cell with different reagents. Epac1-positive astrocytes that overlapped significantly with neighboring cells were excluded from the analysis.

Example 3

This example shows measurements of exocytotic events in cultured astrocytes upon stimulation with ATP and various cAMP elevating agents.

Astrocytes were loaded with 0.1 mg/mL Alexa Fluor$^{546}$-dextran (Molecular Probes, Invitrogen, Eugene, Oreg., USA) for 2 h at 37° C., washed for 2 h, and transferred in a standard saline solution (10 mM Hepes/NaOH, pH 7.2, 10 mM D-glucose, 131.8 mM NaCl, 1.8 mM CaCl$_2$, 2 mM MgCl$_2$, and 5 mM KCl) to the chamber for imaging. Time-lapse confocal images were obtained every 2 s for 10 min with the inverted Zeiss LSM780 and Zeiss LSM510 META confocal microscopes with oil-immersion plan apochromatic objective (63×, 1.4 NA) and 543-nm He—Ne laser excitation. Emission light was acquired with a 560-nm long-pass emission filter. 100 s after the start of recording cells were stimulated with different reagents and their combinations: 1 mM adenosine-5'-triphosphate (ATP; purinergic receptor agonist), 1 µM adrenaline (ADR; α- and β-AR agonist), 10 µM isoproterenol (Iso; β-AR agonist) in a standard saline solution. Cells were scanned by eye for an individual exocytotic event by rapidly replaying the movie in forward and reverse directions. The onset of exocytosis was defined as the first frame showing a significant decrease in Alexa Fluor$^{546}$-dextran. A circular region of interest was centered on the spot where the event occurred, and changes in the fluorescence intensities of Alexa Fluor$^{546}$-dextran were monitored over time.

Example 4

This example shows labeling of cultured astrocytes with antibodies against GPR81 receptor. Astrocytes growing on the cover slips were fixed by 4% paraformaldehyde in phosphate buffer saline for 15 min at room temperature before being treated with 10% goat serum for 1 h at 37° C. Cultures were then stained with primary rat antibodies raised against GPR81 receptor (1:100 dilution, Sigma-Aldrich, St. Louis, Mo., USA) for 2 h at 37° C. After being washed to remove excess primary antibody, the cultures were incubated for 45 min at 37° C. with Alexa Fluor$^{488}$ conjugated secondary antibody (1:600 dilution; Abcam, Cambridge, UK). Excess antibody was removed and cells were treated with SlowFade Gold antifade reagent (Molecular Probes, Invitrogen). Immunolabeled cells were imaged with the inverted Zeiss LSM510 META confocal microscopes with an oil immersion plan apochromatic objective (63×, 1.4 NA; Carl Zeiss, Jena, Germany) using 488-nm Ar-Ion laser excitation. Emission spectra were acquired with a 505-530-nm bandpass emission filter (Alexa Fluor$^{488}$).

Example 5

This example shows Fluo-4 AM measurements of [Ca$^{2+}$]i. in cultured astrocytes upon stimulation with ATP, various cAMP elevating agents, and distilled H$_2$O (hypotonic stimulation to ~60% of control standard extracellular solution osmolarity).

Live astrocytes were incubated for 30 min at room temperature in medium containing 2 µM of fluorescent dye Fluo-4 AM (Molecular Probes, Invitrogen, Eugene, Oreg., USA). Astrocytes were then transferred to dye-free standard saline solution for at least 30 min before experimentation to allow for cleavage of the AM ester group. Time lapse images were obtained every 3.5 s for up to 10 min with the inverted Zeiss LSM780 confocal microscope with oil-immersion plan apochromatic objective (63×, 1.4 NA) and 488-nm Ar-Ion laser excitation. Emission light was acquired with a 505-530-nm bandpass emission filter. Different stimuli were added after 100 s: 1 mM adenosine-5'-triphosphate (ATP; purinergic receptor agonist), 1 µM adrenaline (ADR; α- and β-AR agonist), 10 µM isoproterenol (Iso; β-AR agonist) in a standard saline solution, distilled water for hypotonic stimulation, and combinations of these stimuli. Flou-4 AM intensity was quantified within a region of interest selected for individual cell. Average fluorescence intensity before stimulation of each cell was subtracted from intensities after stimulation (ΔF). Average fluorescence intensity changes normalized to baseline fluorescence intensity (F/F$_0$) were determined for the first 100 s after stimulation.

REFERENCES

Ahmed, K., Tunaru, S., Offermanns, S., GPR109A, GPR109B and GPR81, a family of hydroxy-carboxylic acid receptors, *Trends Pharmacol Sci* 30(2009), pp. 557-562.

Allaman, I., Lengacher, S., Magistretti, P. J., Pellerin, L., A2B receptor activation promotes glycogen synthesis in astrocytes through modulation of gene expression, *Am J Physiol Cell Physiol* 284(2003), pp. C696-704.

Bergersen, L. H., Gjedde, A., Is lactate a volume transmitter of metabolic states of the brain?, *Front Neuroenergetics* 4(2012), p. 5.

Bicknell, R. J., Luckman, S. M., Inenaga, K., Mason, W. T., Hatton, G. I., Beta-adrenergic and opioid receptors on pituicytes cultured from adult rat neurohypophysis: regulation of cell morphology, *Brain Res Bull* 22(1989), pp. 379-388.

Cureton, E. L. et al., A different view of lactate in trauma patients: protecting the injured brain, *J Surg Res* 159 (2010), pp. 468-473.

Hatton, G. I., Luckman, S. M., Bicknell, R. J., Adrenalin activation of beta 2-adrenoceptors stimulates morphological changes in astrocytes (pituicytes) cultured from adult rat neurohypophyses, *Brain Res Bull* 26(1991), pp. 765-769.

Laureys, G. et al., Astrocytic beta(2)-adrenergic receptors: from physiology to pathology, *Prog Neurobiol* 91(2010), pp. 189-199.

Lee, R. K., Araki, W., Wurtman, R. J., Stimulation of amyloid precursor protein synthesis by adrenergic receptors coupled to cAMP formation, *Proc Natl Acad Sci USA* 94(1997), pp. 5422-5426.

Prebil, M., Vardjan, N., Jensen, J., Zorec, R., Kreft, M., Dynamic monitoring of cytosolic glucose in single astrocytes, *Glia* 59(2011), pp. 903-913.

Ros, J., Pecinska, N., Alessandri, B., Landolt, H., Fillenz, M., Lactate reduces glutamate-induced neurotoxicity in rat cortex, *J Neurosci Res* 66(2001), pp. 790-794.

Schurr, A., Payne, R. S., Miller, J. J., Tseng, M. T., Rigor, B. M., Blockade of lactate transport exacerbates delayed neuronal damage in a rat model of cerebral ischemia, *Brain Res* 895(2001), pp. 268-272.

Shain, W., Forman, D. S., Madelian, V., Turner, J. N., Morphology of astroglial cells is controlled by beta-adrenergic receptors, *J Cell Biol* 105(1987), pp. 2307-2314.

Wurm, A. et al., Involvement of A(1) adenosine receptors in osmotic volume regulation of retinal glial cells in mice, *Mol Vis* 15(2009), pp. 1858-1867.

EMBODIMENTS OF THE INVENTION

1. A method for screening a compound useful in reducing cell edema and/or in the treatment of a disease associated with astrocytic cytoplasmic hyperexcitability and/or cytosolic glucose homeostasis, said method comprising:
   (i) providing a compound;
   (ii) bringing said compound in contact with an astrocyte; and
   (iii) determining the cAMP level in said astrocyte contacted with said compound.

2. The method according to item 1, wherein said compound is identified as a compound useful in reducing cell edema and/or in the treatment of a disease associated with astrocytic cytoplasmic hyperexcitability and/or cytosolic glucose homeostasis, if the cAMP level in the astrocyte increases after contact.

3. The method according to item 1 or 2, wherein the cell edema is astroglial edema.

4. The method according to item 1 or 2, wherein said disease associated with astrocytic cytoplasmic hyperexcitability and/or cytosolic glucose homeostasis is a disease selected from the group consisting of epilepsy, intellectual disability, sleep disorders, CNS trauma, cognitive deficit, autism, neuroinflammation, and neurodegenerative disorders, such as multiple sclerosis, Alzheimer's disease, Parkinson's disease, and Huntington's chorea.

5. An agent elevating the cAMP level in astrocytes for use in reducing cell edema and/or in the treatment of a disease associated with astrocytic cytoplasmic hyperexcitability and/or cytosolic glucose homeostasis.

6. The agent for use according to item 5, wherein said agent is an agonist for a G-protein coupled receptor.

7. The agent for use according to item 5 or 6, wherein said agent is an agonist for a β-adrenergic receptor (β-AR).

8. The agent for use according to item 7, wherein said agent is selected from the group consisting of adrenaline (ADR), noradrenalin (NA), dobutamine, dobutamine chloride, isoproterenol (β$_1$ and β$_2$), xamoterol, salbutamol, levosalbutamol, fenoterol, formoterol, metaproterenol, salmeterol, terbutaline, clenbuterol, isoetarine, pirbuterol, procaterol, ritodrine, arbutamine, befunolol, bromoacetylalprenololmenthan, broxaterol, cimaterol, cirazoline, denopamine, dopexamine, etilefrine, hexoprenaline, higenamine, indakaterol, salbutemol, isoxsuprine, mabuterol, methoxyphenamine, nylidrin, oxyfedrine, prenalterol, ractopamine, reproterol, rimiterol, tretoquinol, tulobuterol, zilpaterol, and zinerol.

9. The agent for use according to item 5 or 6, wherein said agent is an agonist for a lactate receptor.

10. The agent for use according to item 9, wherein said agent is an agonist for the lactate receptor GPR81.

11. The agent for use according to item 9 or 10, wherein said agent is selected from the group consisting of lactate, such as D-lactate or L-lactate, hydroxybenzoic acid, such as 3-hydroxy benzoic acid, 3-hydroxy-5-substituted benzoic acid, such as 3-Chloro-5-hydroxybenzoic acid (3-Cl-5-HBA), 3-hydroxy butyrate, 3-hydroxy-yoctanoate, 3H-imidazo[4,5-b]pyridin-5-ol derivatives.

12. The agent for use according to item 5, wherein said agent is a phosphodiesterase (PDE) inhibitor.

13. The agent for use according to item 12, wherein said agent is selected from the group consisting of caffeine, aminophylline, 3-isobutyl-1-methylxanthine, paraxanthine, pentoxifylline, theobromine, theophylline, vinpocetine, erythro-9-(2-hydroxy-3-nonyl)adenine, BAY 60-7550, oxindole, inamrinone, PDP (9-(6-Phenyl-2-oxohex-3-yl)-2-(3,4-dimethoxybenzyl)-purin-6-one), milrinone, enoximone, cilostazol, mesembrine, rolipram, ibudilast, piclamilast, rolipram, luteolin, drotaverine, and roflumilast.

14. The agent for use according to any one of items 5 to 13, wherein the cell edema is astroglial edema.

15. The agent for use according to any one of items 5 to 13, wherein said disease associated with astrocytic cytoplasmic hyperexcitability and/or cytosolic glucose homeostasis is a disease selected from the group consisting of epilepsy, intellectual disability, sleep disorders, CNS trauma, cognitive deficit, autism, neuroinflammation, and neurodegenerative disorders, such as multiple sclerosis, Alzheimer's disease, Parkinson's disease, and Huntington's chorea.

The invention claimed is:

1. A method for screening a compound useful in reducing astroglial edema, said method comprising:
   (i) providing a compound;
   (ii) bringing said compound in contact with an astrocyte; and
   (iii) determining the cAMP level in said astrocyte both before and after contact with said compound using fluorescence resonance energy transfer (FRET); wherein said compound is identified as a compound useful in reducing astroglial edema, if the cAMP level in the astrocyte increases after contact.

2. The method of claim 1, wherein determining the cAMP level using FRET measurement includes transfecting said astrocyte with Epac1-camps or AKAR2.

3. The method of claim 1, further including the steps of:
   (iv) measuring cell area and perimeter of said astrocyte before and after contact of said astrocyte with said compound; and
   (v) comparing the difference in cell area and perimeter of said astrocyte before and after contact with said compound with the measured cAMP level of said astrocyte before and after contact with said compound, wherein said compound is identified as a compound useful in reducing astroglial edema where, along with the cAMP level in the astrocyte having increased after contact, the cell area of said astrocyte has decreased and the perimeter of said astrocyte has increased after contact with said compound as compared to the cell area and perimeter of said astrocyte measured before contact with said compound.

4. The method of claim 3, wherein determining the cAMP level using FRET measurement includes transfecting said astrocyte with Epac1-camps or AKAR2.

* * * * *